United States Patent
Hössel et al.

(12)

(10) Patent No.: US 6,191,188 B1
(45) Date of Patent: Feb. 20, 2001

(54) AQUEOUS COMPOSITIONS AND THEIR USE

(75) Inventors: Peter Hössel, Schifferstadt; Karin Sperling, Neustadt; Volker Schehlmann, Römerberg, all of (DE)

(73) Assignee: BASF Aktiengesellschaft, Ludwishafen (DE)

( * ) Notice: Under 35 U.S.C. 154(b), the term of this patent shall be extended for 0 days.

(21) Appl. No.: 09/331,635

(22) PCT Filed: Dec. 19, 1997

(86) PCT No.: PCT/EP97/07168

§ 371 Date: Jun. 23, 1999

§ 102(e) Date: Jun. 23, 1999

(87) PCT Pub. No.: WO98/31328

PCT Pub. Date: Jul. 23, 1998

(30) Foreign Application Priority Data

Jan. 14, 1997 (DE) ............................................... 197 01 018

(51) Int. Cl.[7] ...................................................... C08L 15/00
(52) U.S. Cl. ........................... 523/105; 424/47; 424/70.15
(58) Field of Search ................................ 524/336, 378; 424/47, 45, 61, 70, 71; 523/105

(56) References Cited

U.S. PATENT DOCUMENTS

| | | | |
|---|---|---|---|
| 3,973,574 | * 8/1976 | Minagawa et al. | 424/71 |
| 4,252,656 | * 2/1981 | Liebowitz et al. | 427/242 |
| 5,037,632 | 8/1991 | Gross et al. | . |
| 5,690,921 | 11/1997 | Lang et al. | . |
| 5,869,032 | * 2/1999 | Tropsch et al. | 424/70.15 |

FOREIGN PATENT DOCUMENTS

| | | | |
|---|---|---|---|
| 2040963 | * 4/1991 | (CA) | 220/12 |
| 155 400 | 9/1985 | (EP) | . |
| 256 691 | 2/1988 | (EP) | . |
| 331 930 | 9/1989 | (EP) | . |
| 455 081 | 11/1991 | (EP) | . |
| 94/08554 | 4/1994 | (WO) | . |

* cited by examiner

*Primary Examiner*—Edward J. Cain
*Assistant Examiner*—Kataryzna Wyrozebski
(74) *Attorney, Agent, or Firm*—Keil & Weinkauf

(57) ABSTRACT

Aqueous preparations comprising
a) from 0.1 to 10% by weight of a copolymer based on N-vinylcaprolactam, N-vinylpyrrolidone and N-vinylimidazole and
b) from 0.1 to 10% by weight of at least one polyoxyethylene $C_6$–$C_{15}$-monoalkyl ether,
and their use in cosmetic formulations are described.

10 Claims, No Drawings

AQUEOUS COMPOSITIONS AND THEIR USE

This is a 371 of application No. PCT/EP97/07168, filed Dec. 19, 1997.

The present invention relates to aqueous preparations and to their use in cosmetic formulations.

Lang et al. in WO 94/08554 describe compositions for setting the hair, comprising at least one polymer and also ethoxylated $C_{12}$–$C_{20}$-fatty alcohols and at least one water-soluble, halogen-free organic solvent. These solvents have the undesirable effect of drying out the hair and thus leading to its embrittlement. They may also be a cause of skin irritation.

EP-B 155 400 describes compositions for setting the hairstyle and caring for the hair, comprising—in addition to a quaternized copolymer of vinylpyrrolidone and dimethylaminoethyl methacrylate—tetraoxyethylene lauryl ether.

EP-B 331 930 likewise describes compositions for setting the hairstyle and caring for the hair, with a copolymer of vinylpyrrolidone and vinylimidazole methochloride and with tetraoxyethylene lauryl ether.

A disadvantage of the composition described above, however, is that it can lead, especially in conditions of high atmospheric humidity, to unnatural stickiness of the hair. Moreover, these compositions also show weaknesses in the setting of hair. Another disadvantage of the copolymers specified in EP-B 155 400 is the comparatively poor dry-combability of the treated hair.

EP-A 715 843 describes aerosol foams with copolymers based on vinylcaprolactam, vinylpyrrolidone and vinylimidazole, an emulsifier such as cetyldimethyl-2-hydroxyethylammonium dihydrogen phosphate or Ceteareth-25® (=polyoxyethlene [sic] cetyl ether) and customary cosmetic auxiliaries, with or without a propellant. The setting effect on hair that is achieved using these aerosol foams, however, is inadequate.

Cosmetic preparations, especially preparations for hair, are intended to have a range of advantageous properties. Examples of major requirements based on such cosmetic compositions are 1. skin compatibility (no irritant or toxic effects on the skin),
2. good feeling on and adhesion to the skin or hair,
3. water resistance,
4. good compatibility with other cosmetic substances,
5. flexible setting of the hair (no stickiness of the hair even with high atmospheric humidity),
6. prevention of electrostatic charging of the hair,
7. provision of a good feel to the hair (good holding, good hair volume and little tackiness),
8. good wet-combability,
9. good flexural strength,
10. enhancement of luster, and
11. good solubility in cosmetic solutions and preparations.

It is an object of the present invention to provide a preparation which meets as many as possible of the advantageous properties and which does not have the disadvantages of the compositions known to date. We have found that this object is achieved by the novel aqueous preparation comprising a) from 0.1 to 10% by weight of a copolymer based on N-vinylcaprolactam, N-vinylpyrrolidone and N-vinylimidazole and b) from 0.1 to 10% by weight of at least one polyoxyethylene $C_6$–$C_{15}$-monoalkyl ether.

Advantageous copolymers (a) are all those which include N-vinylcaprolactam, N-vinylpyrrolidone and N-vinylimidazole. Suitable polymers are preferably those obtainable by free-radically initiated copolymerization of monomer mixtures comprising ($a_1$) from 20 to 80% by weight, preferably from 40 to 60% by weight, of N-vinylcaprolactam, ($b_1$) from 10 to 60% by weight, preferably from 20 to 50% by weight, of N-vinylpyrrolidone, ($c_1$) from 5 to 50% by weight, preferably from 7 to 20% by weight, of an N-vinylimidazole or quaternized N-vinylimidazole, and ($d_1$) from 0 to 30% by weight, preferably from 0 to 50% by weight, of a further free-radically copolymerizable monomer whose homopolymer has a glass transition temperature of more than 20° C.

and, where the monomer ($c_1$) employed is a nonquaternized N-vinylimidazole, advantageously by subsequent quaternization of the polymer.

Suitable N-vinylimidazoles (monomers ($c_1$) are 1-vinylimidazole derivatives of the general formula I,

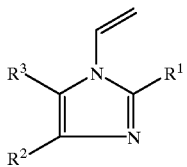

where $R^1$ is hydrogen, $C_1$–$C_4$-alkyl or phenyl and $R^2$ and $R^3$ are identical or different and are hydrogen or $C_1$–$C_4$-alkyl.

The vinylimidazoles can be employed as free bases or in quaternized form, the copolymerization of quaternized vinylimidazoles being preferred. If the vinylimidazoles are employed in the copolymerization in the form of the free bases, then it is advantageous to conduct quaternization after the polymerization.

Examples of compounds suitable for quaternizing the vinylimidazole are $C_1$–$C_{22}$-alkyl halides, for example methyl chloride, bromide and iodide, ethyl chloride and bromide, propyl, hexyl, dodecyl and lauryl chlorides and benzyl halides, especially the chloride and the bromide. Further suitable quaternizing agents are dialkyl sulfates, especially dimethyl or diethyl sulfate. The vinylimidazoles can also be quaternized with alkylene oxides, such as ethylene or propylene oxide, in the presence of acids. Preferred quaternizing agents are methyl chloride, dimethyl sulfate and diethyl sulfate. Further particularly preferred monomers of group ($c_1$) are 3-methyl-1-vinylimidazolium chloride and 3-methyl-1-vinylimidazolium methyl sulfate. The quaternization of the monomers or of a polymer with one of the abovementioned quaternizing agents can be performed by methods which are general knowledge.

Examples of suitable monomers ($d_1$) are $C_1$–$C_{12}$-alkyl acrylates or methacrylates, such as tert-butyl acrylate, isobutyl methacrylate, n-butyl methacrylate, methyl methacrylate, ethyl methacrylate, t-butyl methacrylate, isobornyl acrylate or isobornyl methacrylate, or acrylamides, such as N-tert-butylacrylamide or N-tert-octylarylamide [sic]. Also suitable are monomers whose solubility in water at 25° C. is more than 5% by weight, examples being acrylic, methacrylic and crotonic acid, N-methylolmethacrylamide, N-vinyl-N-methylacetamide, N-vinylformamide, acrylamide, N,N-dimethylacrylamide, methacrylamide, N-vinyloxazolidone, N-vinyltriazole, hydroxyalkyl(meth)

acrylates or alkylethylene glycol(meth)acrylates having 1–50 ethylene glycol units in the molecule.

Very particularly preferred copolymers are those of (a) from 5 to 30% by weight of 3-methyl-1-vinylimidazolium methyl sulfate, (b) from 40 to 60% by weight of N-vinylcaprolactam, and (c) from 30 to 50% by weight of N-vinylpyrrolidone.

The polymers can be prepared by the conventional techniques of free-radically initiated polymerization. They are preferably prepared by solution polymerization in solvents such as water, methanol, ethanol, isopropanol or a mixture thereof. The amounts of monomers and solvents are judiciously chosen so as to give solutions with concentrations of from 15 to 60% by weight. Polymerization is normally conducted at from 60° C. to 130° C. under atmospheric or the autogenous pressure.

Initiators that can be employed for the free-radical polymerization are the customary peroxo and/or azo compounds, examples being dibenzoyl peroxide, tert-butyl perpivalate, tert-butyl 2-ethylhexanoate, di-tert-butyl peroxide, tert-butyl hydroperoxide, azobisisobutyronitrile, azobis(2-amidinopropane)dihydrochloride or 2,2'-azobis(2-methylbutyronitrile). Also suitable are initiator mixtures or customary redox initiators. The initiators can be employed in the usual amounts, for example from 0.05 to 5% by weight based on the amount of monomers to be polymerized.

The molecular weight can be adjusted if desired by adding regulators, for example compounds containing sulfur in bonded form.

The K values of the polymers should be from 10 to 350, preferably from 50 to 300. The particular K value desired can be established in a conventional manner by choosing the polymerization conditions, for example the period of polymerization and the concentrations of initiator and regulator. The K values are measured by the method of Fikentscher, Cellulosechemie, 13, (1932) 58–64 at 25° C. in a 0.1% strength by weight aqueous solution.

In the aqueous cosmetic composition the copolymers are used in an amount of from 0.1 to 10% by weight, preferably from 0.1 to 5% by weight and, with very particular preference, from 0.5 to 2.5% by weight.

By ethoxylated alkyl ethers (=polyoxyethylene $C_6$–$C_{15}$-monoalkyl ethers) are meant compounds of the formula

$$CH_3(CH_2)_m(OCH_2CH_2)_nOH \qquad (II)$$

where m is 5 to 14, preferably 7 to 11, more preferably 9 to 11, and n is 1 to 30, examples being polyoxyethylene caproyl, caprylyl, pelargonyl, capryl, lauryl or myristyl ethers. These compounds are available under various trade names, for example the Brij® grades, or can be synthesized by ethoxylating fatty alcohols such as 1-hexanol (=caproyl alcohol), 1-heptanol (=enanthyl alcohol), 1-octanol (=caprylyl alcohol), 1-nonanol (=pelargonyl alcohol), 1-decanol (=carpryl [sic] alcohol), 1-undecanol, 1-dodecanol (=lauryl alcohol), 1-tridecanol, 1-tetradecanol (=myristyl alcohol) or 1-pentadecanol. The degree of ethoxlation [sic] of the various alkyl ethers here may vary greatly. The degrees of ethoxylation (n) are preferably from 1 to 25, particularly preferably from up to [sic] 1 to 20 and, with very particular preference, from 1 to 10. Branched-chain ethoxylated alkyl ethers such as isolaureth-3, isolaureth-6 or isolaureth-10 (prepared using branched $C_{12}$ alcohols) are also suitable.

It is advantageous to use polyoxyethylene caproyl, caprylyl, pelargonyl, capryl, lauryl or myristyl ether. Preference is given to polyoxyethylene caprylyl, pelargonyl, lauryl or myristyl ether. The polyoxyethylene lauryl ethers are particularly preferred, while very particular preference is given to polyoxyethylene (4) lauryl ether, which is marketed under the trade name Brij® 30 or Laureth-4®, polyoxyethylene (3) lauryl ether (=laureth-3) or isolaureth-6.

It is preferred to use alkyl ethers having an HLB (hydrophilic-lipophilic balance) value of from 1 to 20, preferably from 10 to 20.

The ethoxylated alkyl ethers of higher fatty alcohols such as, for example, cetyl, stearyl, oleyl or linolyl alcohol give much poorer flexural strengths of the hair after treatment than the shorter-chain fatty alcohols specified above.

The ethoxylated alkyl ethers are added to the aqueous cosmetic composition advantageously in a concentration of from 0.1 to 10% by weight, with particular preference from 0.1 to 5% by weight and, with very particular preference, in a concentration of from 0.1 to 1% by weight.

The novel aqueous cosmetic compositions may additionally and advantageously comprise at least one further film-forming polymer. Examples of suitable polymers are customary film-forming polymers of natural or synthetic origin.

Examples of synthetic polymers are homo- or copolymers of acrylic or methacrylic acid, copolymers of acrylic and/or methacrylic acid with acrylamides, copolymers of acrylic and/or methacrylic acid with alkyl (methacrylates) [sic], copolymers based on alkyl vinyl ethers and monoalkyl maleates and/or esters of other carboxylic acids, such as itaconic acid or fumaric acid, copolymers of octylacrylamide, acrylate and butylaminoethyl methacrylate, and also vinylpyrrolidone homo- or copolymers, homo- or copolymers of N-vinylcarboxamides with other vinylmonomers, vinylpyrrolidone-vinyl acetate copolymers or copolymers of vinylpyrrolidone, vinyl acetate, vinyl propionate and/or further vinyl monomers. Mixtures of the abovementioned polymers are also suitable.

Examples of natural polymers are gelatin, pectins, galactomannans, shellac, alginate, chitosans, cellulose or derivatives thereof. Also suitable are mixtures of the natural polymers with one another or with the synthetic polymers.

The novel aqueous cosmetic composition comprises the abovementioned film-forming polymers, if desired, in an amount of from 0.1 to 10% by weight, preferably from 0.5 to 5% by weight.

In the case of use in pressurized containers the novel composition may also include a propellant. Examples of suitable propellants are n-butane, isobutane, propane, difluorodichloromethane, trichloromonofluoromethane, tetrafluorodichloroethane, dimethyl ether, $N_2$, $N_2O$, $CO_2$ and compressed air or mixtures thereof.

The propellants are preferably added to the novel cosmetic composition in an amount of up to 30% by weight, preferably from 2 to 10% by weight.

However, the novel composition can also be used without a propellant, in pump applicators.

The novel cosmetic composition may include organic solvents, preferably water-soluble organic solvents of which examples are lower aliphatic alcohols such as ethanol, propanol or isopropanol, glycols such as ethylene glycol, propylene glycol or polyglycols thereof, polyethylene glycol alkyl ethers of $C_1$–$C_4$ alcohols, simple or mixed ketones of $C_1$–$C_5$ alcohols, such as acetone or methyl ethyl ketone, preference being given to glycols, polyglycols and polyethylene glycol alkyl ethers.

The novel aqueous cosmetic composition may additionally comprise customary cosmetic additives, such as colorants, fragrances, surfactants, protein hydrolysates, re-oiling agents, thickeners, luster additives, UV absorbers, herb extracts, preservatives, such as bactericides or fungicides, emulsifiers, such as sorbitan fatty acid esters or lanolin derivatives, stabilizers, such as magnesium or aluminum salts of fatty acids, complexing agents such as EDTA, and antioxidants such as BHT, BHA, ascorbic acid or alpha-tocopherol.

Further possible constituents of the novel cosmetic compositions can be cosmetic active substances such as panthenol, bisabolol, alpha-tocopherol, alpha-tocopherol acetate, aloe vera, seaweed extract and/or hyaluronic acid.

The novel polymers are suitable for use as active substances in cosmetic formulations and preparations, whether cosmetic skin preparations such as liquid soaps, body lotions, shaving lotions, face lotions and other cosmetic lotions, but especially in cosmetic hair preparations such as hair treatment compositions, hair lotions, hair rinses, hair emulsions, treatment fluids for damaged ends, equalizing agents for permanent waves, hot oil treatment preparations, conditioners, setting lotions or hairsprays. Depending on the field of use the novel aqueous cosmetic compositions can be present in preparations used in the form of solutions, rinses, lotions, mousses, gels, aerosol foams, pump foams, or sprays.

EXAMPLES

| Formulation | |
|---|---|
| 2.00 g | of polymer active substance |
| 0.20 g | of foam forming |
| 0.10 g | of Euxyl K 100* |
| 0.40 g | of perfume oil Carina/Cremophor RH 40 1:3 |
| ad 100 | distilled water. |

*Euxyl K 100 is a preservative comprising benzyl alcohol, methyl chloroisothiazolinone and methylisothiazolone

| No. | Polymer | Foam former (INCI name) | Setting: subjective assessment on one lock of hair | Flexural strength (cN) |
|---|---|---|---|---|
| 1 | Luviquat ® Hold[1] | Laureth-4 ® | rating 1 | 390 |
| 2 | Luviquat ® Hold[1] | Hydroxyethyl-cetyldimonium phosphate | rating 2 | 170 |
| 3 | Luviquat ® Hold[1] | Ceteareth-25 ® | rating 2 | 330 |

[1]Terpolymer based on 50% by weight N-vinylcaprolactam, 40% by weight N-vinylpyrrolidone and 10% by weight N-vinylimidazolium methyl sulfate Description of Test Methods Pretreating the locks of hair Locks of hair 20 cm long and weighing from 2.2 to 2.6 g are soaked in the above formulation, pressed gently against filter paper, and dried overnight at 20° C. and 65% relative humidity.

Assessing the setting effect on a lock of hair

Assessment is made subjectively by flexing the locks of hair with the fingers of one hand. Rating 1: very good setting; rating 2: good setting, rating 3: poor setting.

Flexural strength

The lock of hair is placed symmetrically on two cylindrical rollers (diameter 6 mm, 9 cm apart). At a point central between the two points of contact of the hair with the rollers, a tensile pressure tester is used to exert an increasing force on the lock of hair. The maximum force before the treated lock of hair folds is indicated in centinewtons (cN). It is a measure of the setting effect of polymers on hair. Each polymer solution was tested on 10 different locks of hair.

We claim:

1. An aqueous composition comprising
   a) from 0.1 to 10% by weight of a copolymer based on N-vinylcaprolactam, N-vinylpyrrolidone and N-vinylimidazole and
   b) from 0.1 to 10% by weight of at least one polyoxyethylene $C_6$–$C_{15}$-monoalkyl ether.

2. The composition of claim 1, wherein the amount of copolymer is from 0.1 to 5.0% by weight.

3. The composition of claim 1, wherein the amount of polyoxyethylene $C_6$–$C_{15}$-monoalkyl ether is from 0.1 to 5.0% by weight.

4. The composition of claim 1, wherein the polyoxyethylene monoalkyl ether is a polyoxyethylene $C_6$–$C_{12}$-monoalkyl ether.

5. The composition of claim 4, wherein the polyoxyethylene monoalkyl ether is polyoxyethylene lauryl ether.

6. The composition of claim 1, further comprising at least one film-forming polymer.

7. The composition of claim 1, further comprising up to 30% by weight of a propellant selected from the group consisting of n-butane, isobutane, propane, difluorodichloromethane, trichloromonofluoromethane, tetrafluorodichloroethane, dimethyl ether, $N_2$, $N_2O$, $CO_2$, compressed air and a mixture thereof.

8. The composition of claim 6, further comprising up to 30% by weight of a propellant selected from the group consisting of n-butane, isobutane, propane, difluorodichloromethane, trichloromonofluoromethane, tetrafluorodichloroethane, dimethyl ether, $N_2$, $N_2O$, $CO_2$ and compressed air.

9. A process for increasing the flexural strength of hair, which process comprises applying to the hair an effective amount of an aqueous composition comprising
   a) from 0.1 to 10% by weight of a copolymer based on N-vinylcaprolactam, N-vinylpyrrolidone and N-vinylimidazole and
   b) from 0.1 to 10% by weight of at least one polyoxyethylene $C_6$–$C_{15}$-monoalkyl ether.

10. A process for improving the setting of hair, which process comprises applying to the hair an effective amount of an aqueous composition comprising
   a) from 0.1 to 10% by weight of a copolymer based on N-vinylcaprolactam, N-vinylpyrrolidone and N-vinylimidazole and
   b) from 0.1 to 10% by weight of at least one polyoxyethylene $C_6$–$C_{15}$-monoalkyl ether.

* * * * *